United States Patent
Cummins

(10) Patent No.: US 7,108,709 B2
(45) Date of Patent: Sep. 19, 2006

(54) SURGICAL STAPLE

(76) Inventor: Christy Cummins, 9 Furnes Manor, Johnstown, Naas, County Kildare (IE)

( * ) Notice: Subject to any disclaimer, the term of this patent is extended or adjusted under 35 U.S.C. 154(b) by 239 days.

(21) Appl. No.: 10/240,183

(22) PCT Filed: Jun. 4, 2002

(86) PCT No.: PCT/IE02/00078

§ 371 (c)(1),
(2), (4) Date: Jan. 22, 2003

(87) PCT Pub. No.: WO02/098302

PCT Pub. Date: Dec. 12, 2002

(65) Prior Publication Data

US 2004/0028502 A1 Feb. 12, 2004

(30) Foreign Application Priority Data

Jun. 7, 2001 (IE) .......................................... S2001/0547

(51) Int. Cl.
*A61B 17/04* (2006.01)

(52) U.S. Cl. ........................................ 606/219; 606/215

(58) Field of Classification Search ................. 606/219, 606/215, 143, 157, 158; 411/460
See application file for complete search history.

(56) References Cited

U.S. PATENT DOCUMENTS

| | | | | |
|---|---|---|---|---|
| 2,684,070 A | * | 7/1954 | Kelsey ........................ | 606/221 |
| 3,482,428 A | | 12/1969 | Kapitanov et al. | |
| 4,014,492 A | | 3/1977 | Rothfuss | |
| 4,428,376 A | * | 1/1984 | Mericle ........................ | 606/219 |
| 4,505,273 A | * | 3/1985 | Braun et al. ................. | 606/219 |
| 4,523,695 A | | 6/1985 | Braun et al. | |
| 4,610,251 A | | 9/1986 | Kumar | |
| 4,610,252 A | * | 9/1986 | Catalano ..................... | 606/157 |
| 4,724,840 A | | 2/1988 | McVay et al. | |
| 4,771,782 A | | 9/1988 | Millar | |
| 4,789,090 A | | 12/1988 | Blake, III | |
| 4,874,122 A | * | 10/1989 | Froelich et al. ............... | 227/19 |
| 5,108,421 A | * | 4/1992 | Fowler ........................ | 606/213 |
| 5,147,381 A | | 9/1992 | Heimerl et al. | |
| 5,192,300 A | * | 3/1993 | Fowler ........................ | 606/213 |
| 5,246,443 A | | 9/1993 | Mai | |

(Continued)

FOREIGN PATENT DOCUMENTS

| | | |
|---|---|---|
| DE | 297 23 736 U 1 | 4/1999 |
| EP | 0 386 361 | 9/1990 |
| EP | 0 756 851 | 2/1997 |
| EP | 0 774 237 | 5/1997 |
| EP | 0 941 697 | 9/1999 |
| FR | 2 443 238 | 7/1980 |
| GB | 1 358 466 | 7/1974 |
| GB | 2 075 144 | 11/1981 |
| WO | WO 97/20505 | 6/1997 |
| WO | WO 98/17179 | 4/1998 |
| WO | WO 98/25508 | 6/1998 |
| WO | WO 00/56228 | 9/2000 |

OTHER PUBLICATIONS

XP–002199926, dated Sep. 8, 2000, Anthony et al.

Primary Examiner—Gary Jackson
(74) Attorney, Agent, or Firm—Nutter, McClennen & Fish LLP

(57) ABSTRACT

A generally U-shaped surgical staple comprises a base 10 and a pair of generally "L"-shaped legs 12 extending substantially perpendicularly from opposite ends of the base respectively. The legs 12 in use of the staple are bent through approximately 90° relative to the base. To effect a greater compression of the stapled tissue the legs include a penetrative portion 16 adjacent the tip and a compressive structure 30 which, due to its increased height relative to that of the penetrative portion, spreads the compressive forces of the staple further along the length of the incision being closed. The compressive portion also provides a depth stop to avoid the tip penetrating too deeply into the tissue in which it is deployed.

24 Claims, 7 Drawing Sheets

U.S. PATENT DOCUMENTS

| | | | |
|---|---|---|---|
| 5,275,616 A * | 1/1994 | Fowler | 606/213 |
| 5,292,309 A | 3/1994 | Van Tassel et al. | |
| 5,292,332 A | 3/1994 | Lee | |
| 5,366,479 A * | 11/1994 | McGarry et al. | 606/219 |
| 5,395,030 A | 3/1995 | Kuramoto et al. | |
| 5,431,639 A | 7/1995 | Shaw | |
| 5,443,481 A * | 8/1995 | Lee | 606/213 |
| 5,470,010 A | 11/1995 | Rothfuss et al. | |
| 5,474,557 A * | 12/1995 | Mai | 606/78 |
| 5,478,352 A * | 12/1995 | Fowler | 606/213 |
| 5,527,322 A | 6/1996 | Klein et al. | |
| 5,536,251 A | 7/1996 | Evard et al. | |
| 5,560,532 A | 10/1996 | DeFonzo et al. | |
| 5,591,205 A * | 1/1997 | Fowler | 606/213 |
| 5,601,602 A * | 2/1997 | Fowler | 606/213 |
| 5,620,461 A * | 4/1997 | Muijs Van De Moer et al. | 606/213 |
| 5,643,318 A | 7/1997 | Tsukernik et al. | |
| 5,645,566 A * | 7/1997 | Brenneman et al. | 606/213 |
| 5,674,231 A | 10/1997 | Green et al. | |
| 5,676,689 A * | 10/1997 | Kensey et al. | 606/213 |
| 5,716,375 A * | 2/1998 | Fowler | 606/213 |
| 5,810,846 A | 9/1998 | Virnich et al. | |
| 5,855,312 A | 1/1999 | Toledano | |
| 5,861,005 A | 1/1999 | Kontos | |
| 5,984,949 A | 11/1999 | Levin | |
| 6,004,341 A * | 12/1999 | Zhu et al. | 606/198 |
| 6,007,563 A * | 12/1999 | Nash et al. | 606/213 |
| 6,022,372 A * | 2/2000 | Kontos | 606/219 |
| 6,048,358 A * | 4/2000 | Barak | 606/213 |
| 6,056,768 A * | 5/2000 | Cates et al. | 606/213 |
| 6,090,130 A * | 7/2000 | Nash et al. | 606/213 |
| 6,197,042 B1 * | 3/2001 | Ginn et al. | 606/213 |
| 6,277,140 B1 * | 8/2001 | Ginn et al. | 606/213 |
| 6,322,580 B1 * | 11/2001 | Kanner | 606/213 |
| 6,348,064 B1 * | 2/2002 | Kanner | 606/219 |
| 6,506,210 B1 * | 1/2003 | Kanner | 606/213 |
| 6,533,762 B1 * | 3/2003 | Kanner et al. | 604/175 |
| 6,616,686 B1 * | 9/2003 | Coleman et al. | 606/219 |
| 6,623,510 B1 * | 9/2003 | Belef et al. | 606/213 |
| 6,719,777 B1 * | 4/2004 | Ginn et al. | 606/213 |
| 6,755,842 B1 * | 6/2004 | Kanner et al. | 606/139 |
| 6,767,356 B1 * | 7/2004 | Kanner et al. | 606/213 |
| 2002/0051921 A1 * | 5/2002 | Morita et al. | 430/78 |
| 2003/0097140 A1 * | 5/2003 | Kanner | 606/142 |
| 2003/0109890 A1 * | 6/2003 | Kanner et al. | 606/139 |
| 2004/0010285 A1 * | 1/2004 | Carley et al. | 606/213 |
| 2004/0254591 A1 * | 12/2004 | Kanner et al. | 606/139 |
| 2004/0267312 A1 * | 12/2004 | Kanner et al. | 606/219 |

\* cited by examiner

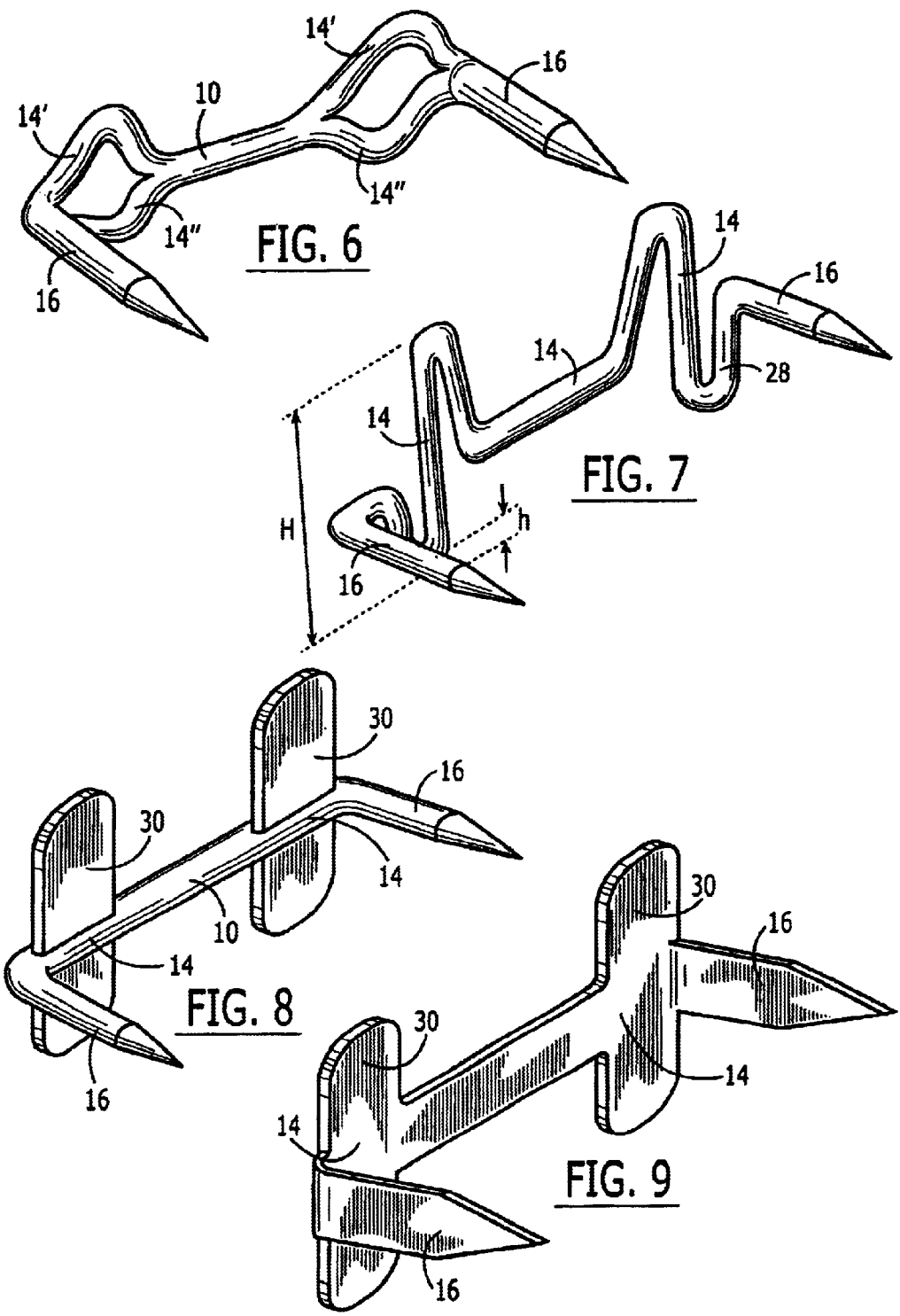

SURGICAL STAPLE

This invention relates to a surgical staple.

Staples have been used in general surgery for many years, mainly for anastomosing tissue. Examples include skin staplers used to close a skin incision in place of the standard manual suturing process, and end-to-end and end-to-side bowel stapling instruments which are generally one shot devices used during bowel reconstruction procedures.

The staples used with these devices are generally manufactured from a metal or metal alloy material such as stainless steel or titanium. The majority are constructed from round profile wire and generally produced in a generally 'U'-shaped configuration. The ends of the 'U'-shape are normally pointed or sharpened so as to ensure easy tissue penetration. Examples of prior art in this area include U.S. Pat. Nos. 4,505,273, 5,026,390 and 4,719,917.

In clinical use the staples are delivered using a stapler device which generally consists of an anvil component positioned inside the 'U' between staple legs and in contact with the staple. A former component is positioned on the other side of the staple base, the gap between the forming arms of the former being approximately the width of the anvil plus two times the diameter of the staple wire. The head of the stapler device is normally positioned centrally across the slit or opening which is to be closed.

On activation of the device the staple legs are advanced forward so that they penetrate the tissue on both sides of the slit or opening. As the former is advanced further the legs of the staple bend around the anvil causing the tips of the legs to advance along an arcuate path toward each other so that the staple ultimately assumes a generally rectangular shape thereby compressing the tissue which has been trapped between the staple legs. This compression of tissue is the mechanism by which a closure is effected. Depending on the length of the incision or opening a series of staples will be delivered along its length in order to ensure a blood tight closure.

While this method of closing an incision is effective when a series of staples are used along the length of, the incision it is less effective when it is desirable to close the opening with the minimum number of staples. For example for an incision of 5–6 mm in length one round wire staple positioned centrally along the incision is insufficient to effect a closure as the compression due to the staple legs only acts in a limited area towards the centre of the incision, leaving the extremities open.

Also in situations where the tissue is soft and friable the narrow staple leg will have a tendency to tear through the tissue as they are bent around the anvil thereby decreasing the level of compression between the staple legs and causing unnecessary damage to the vessel wall.

In order to avoid complications such as clot formation, it is important to retain the staple legs within the vessel wall, i.e. avoid the penetration of the internal wall on the introduction of a foreign body into the lumen of the vessel. If the staple legs penetrate into the lumen of the vessel there is the added danger that excessive pressure from the staple gun may cause the vessel to collapse, which can lead to the legs penetrating the opposing vessel wall, i.e. stapling the vessel walls together and blocking the lumen of the vessel.

Therefore there is a need for an improved surgical staple which will more effectively close an incision, thereby requiring fewer staples to close an incision. In addition it would be advantageous to profile the staple legs so that they are less inclined to tear through softer tissue. Furthermore, it would be desirable to limit the depth of penetration of the staple legs to prevent the legs entering the lumen of the vessel.

Accordingly, the present invention provides a surgical staple comprising a base and a pair of legs each extending from an opposite end of the base, each leg having a penetrative portion terminating at a tip, the staple being deformable to bend each leg relative to the base causing each tip to approach the other leg along a substantially arcuate path lying in a plane, wherein each leg further comprises a compressive portion located intermediate the base and the penetrative portion, the compressive portion having a height greater than that of the penetrative portion, said heights being measured in the direction perpendicular to the plane defined by the arcuate path.

The advantage of the invention is that the improved surgical staple delivers a significantly increased area of compression between the staple legs once the staple has been deformed in use. The increased area of compression is achieved by providing the compression portion which tends to increase the contact area between the staple and the tissue against which it is bearing.

The invention is particularly useful in applications where the staple is permanently implanted inside the body. In such cases it is desirable to minimise the amount of metal which is needed to effect a positive closure. With existing stapler devices a series of staples need to be positioned along the length of the slit or tissue edges being anastomosed. Staples are normally positioned close together as any one staple will only compress a small amount of tissue on either side. Using staples with an improved compression capacity, as provided by this invention, will mean that a significantly lower number of staples is required to close any one incision.

The invention also has particular relevance in the area of vascular puncture closure. During this percutaneous procedure it is desirable to close the arterial puncture preferably with one staple. Again it is desirable that the staple contains the minimum amount of metal. However, it is important that once delivered the staple has generated enough compression along the length of the slit or hole to prevent any blood leakage. The direction of height of the compression portion normal to the plane of closure of the legs corresponds in use to the direction of length along the incision.

Embodiments of the invention will now be described, by way of example, with reference to the accompanying drawings, in which:

FIGS. 5 to 9 are perspective views of embodiments of the invention.

Figure 1:
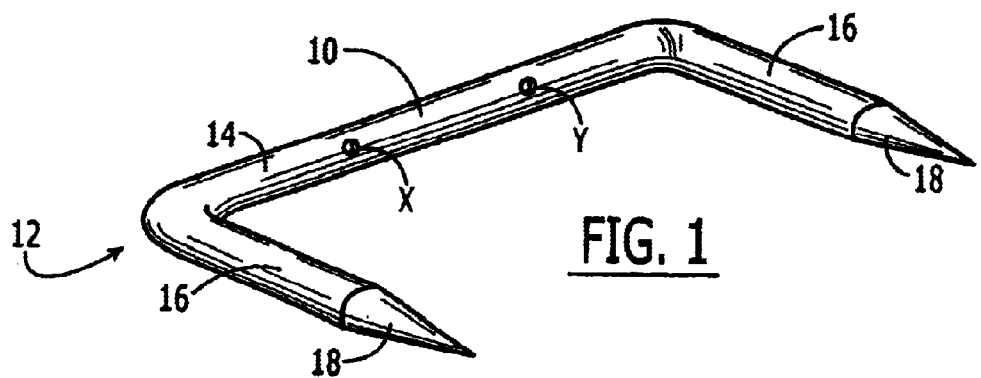
FIG. 1 is a perspective view of a conventional surgical staple.

FIGS. 11 and 12, FIGS. 13 and 14, and FIGS. 15 and 16, respectively, are further perspective views of three additional embodiments of staple, each shown before and after forming.

In the figures the same reference numerals have been used to indicate the same or equivalent components.

Referring first to FIG. 1, a conventional round wire surgical staple is of a generally 'U'-shaped configuration, consisting of a base 10 and a pair of "L"-shaped legs 12 each having a proximal portion 14 forming a linear extension of the base before use (as shown in FIG. 1) and a distal portion 16 projecting substantially perpendicularly from the proximal portion.

The free ends 18 of the staple legs are generally sharpened so as to ensure easy tissue penetration. In addition to penetrating the tissue the staple is also formed in use, to bring the free ends of the legs together and thereby hold closed a wound. By forming the staple, the staple is transformed from a generally "U"-shaped configuration to a generally rectangular shaped configuration during the delivery process. This occurs by bending the legs 12 through 90° relative to the base 10 of the staple at the point where the proximal portions of the legs meet the base (known as the bend points and denoted as points X and Y in the drawings) at points relative to the central portion 10b.

Figure 2A:
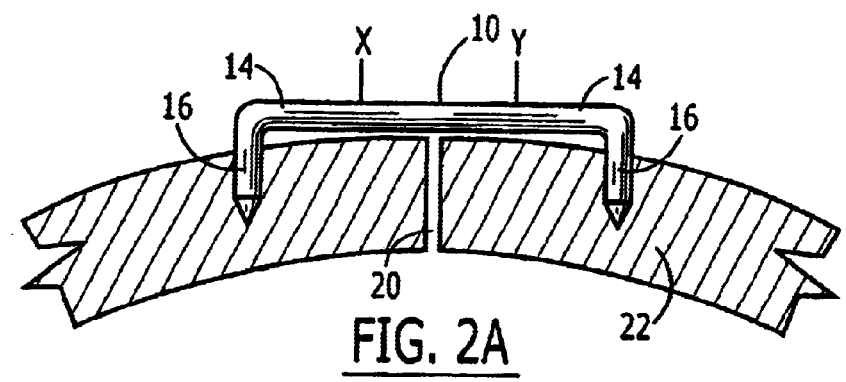
FIG. 2a is a sectional view of an unformed staple in a vessel wall.
Figure 2B:
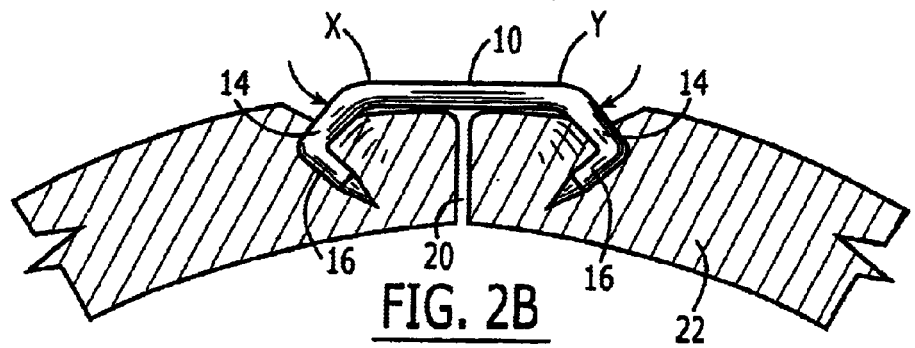
FIG. 2b is a sectional view of a partially formed staple in a vessel wall.
Figure 2C:
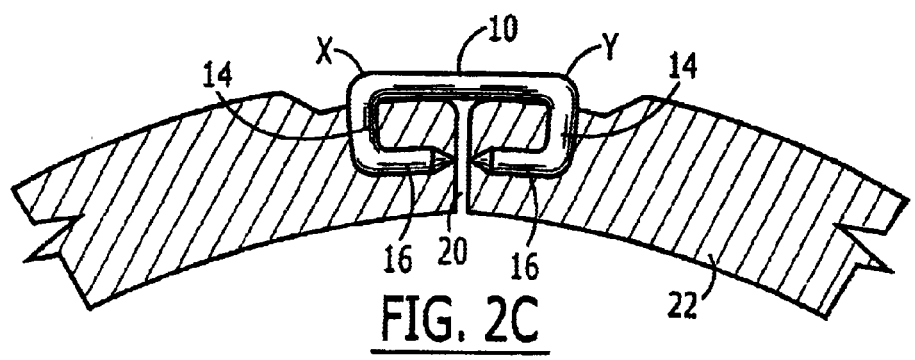
FIG. 2c is a sectional view of a staple fully formed in a vessel wall.

FIGS. 2(a) to 2(c) are a sequence of views showing the process by which the conventional staple is deployed and deformed from a generally "U"-shape to a generally rectangular shape to effect a closure of a puncture hole or slit 20 in a vessel or other tissue 22. In FIG. 2a the staple has been advanced from the delivery device (not shown) such that the distal portions of the staple legs 16 have punctured the tissue 22 and the staple base 10 and proximal portions 14 are lying against the outer surface of the tissue. In FIG. 2b the forming process has begun and the staple is being deformed around bend points X and Y causing the proximal portions 14 and distal portions 16 to arc through an angle of approximately 90° thereby compressing the tissue which is being captured between both staple legs. In FIG. 2c the staple has been fully formed into a rectangular shape, the tissue contained within the rectangle being compressed as a result of the staple legs having arced through approximately 90°.

Figure 3A:
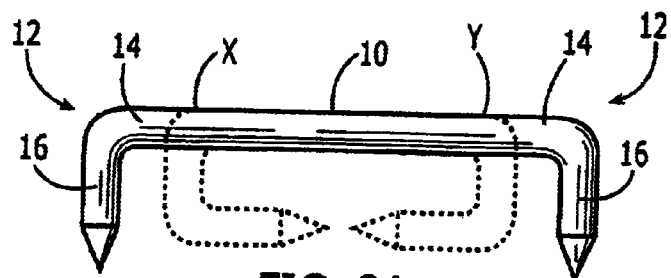
FIG. 3a is a plan view of a staple before and after forming.
Figure 3B:
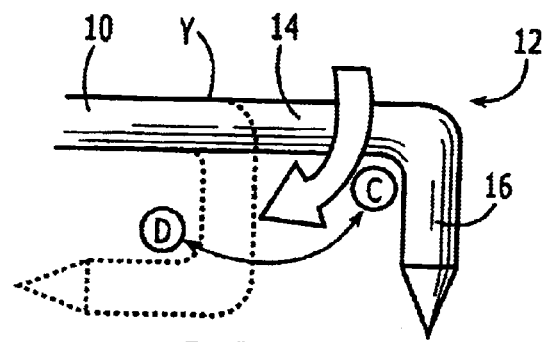
FIG. 3b is an enlarged view of a staple leg before and after forming.

In FIGS. 3a and 3b, the staple is shown prior to forming (dashed lines) and after forming (solid lines). As seen particularly in FIG. 3b, it can be seen that prior to forming and following penetration of the staple leg 12 into the tissue wall that there is an area of tissue captive in the region (c). After the forming process, i.e. when proximal portion 14 and distal portion 16 have arced through 90° at the bend point Y, the tissue which was previously captive at point (c) has now moved to point (d). The same process of compression occurs on the opposite leg of the staple thereby creating compressed tissue 24 (FIG. 4) within the rectangular shape of the formed staple.

Figure 4:
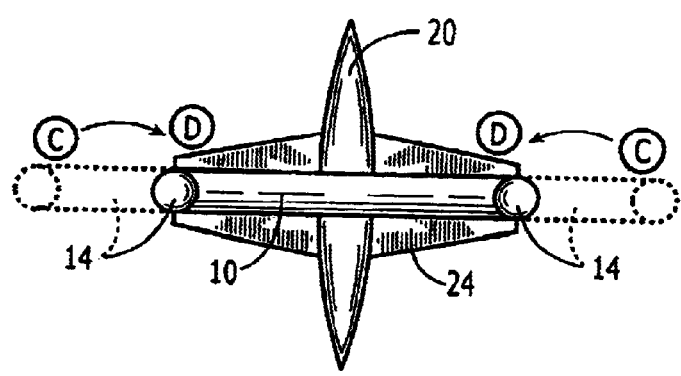
FIG. 4 is a plan view of a staple in position across a tissue opening.

In FIG. 4, the same compression process can be seen in plan view, the tissue which was captive inside the legs 12 at points (c) prior to forming has been moved to point (d) as a result of the staple forming process. However, the level of compression which has transferred to the hole 16 in the tissue is related to the area of surface contact between the staple leg and the tissue at points (c) and (d). With conventional round wire staples this contact area is quite small and therefore delivers a limited amount of compression over the length of the hole opening or slit in the tissue. Also, with round wire and leg to cut its way through softer tissue as opposed to compressing the tissue ahead of it.

The invention solves this problem by increasing the height of a portion of the legs 12 (i.e. the height being the dimension perpendicular to the plane in which the staple legs bend during forming), in order to increase the effective contact area between the staple legs and the tissue as the staple is being deformed. Increasing the contact area in this way will help prevent the staple leg from tearing its way through the tissue but more importantly will create a much greater area of compression within the rectangle of the formed staple and radiating from it, so that this compression will be transferred over a much greater length of the slit or opening 20 in the tissue.

Figure 5:
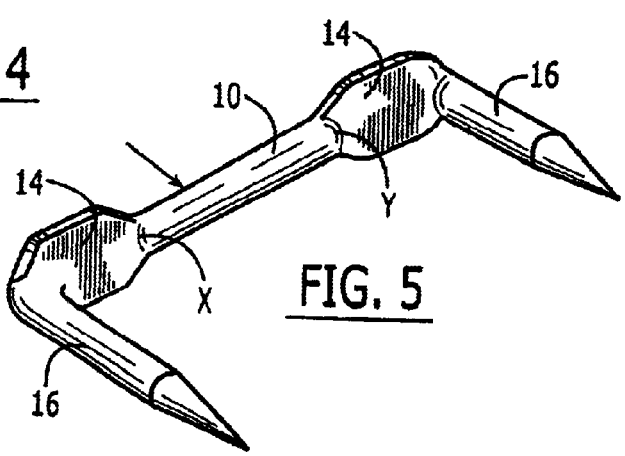

FIG. 5 is a perspective view of a first embodiment of surgical staple according to the invention. Here the proximal portion 14 of the legs of the conventional round wire staple described above have been deformed from a round to a flat, rectangular cross-section, providing a compressive portion located between the penetrative portion of the legs (which in this case is the entire proximal portion 16). As mentioned, the purpose of this compressive portion is to increase the surface contact area between the staple legs and tissue in the direction in which the tissue is being compressed as the staple leg arcs through approximately 90° at its bend point.

FIG. 6 shows another embodiment, in which the staple legs have been divided along the axis of the proximal portions and the opposite divisions 14' and 14" deformed apart so as to significantly increase the overall height of the proximal portions of the legs.

In FIG. 7 another round wire embodiment of the staple is shown. In this staple the wire in the proximal portion 14 of each leg is bent sinusoidally out of alignment with the base 10 to provide a compressive portion whose height H is significantly greater than the height h of the penetrative portion of the leg 16, again for the purpose of increasing the area of compression, and preventing the proximal portion from entering the wound. In the latter regard, it can be seen that the leading section 28 of the sinusoidally bent proximal portion extends generally at right angles from the penetrative portion 16. This provides a slightly rounded step or shoulder to act as a depth stop, defining the end of the penetrative portion of the leg and the start of the compressive portion.

FIG. 8 shows an embodiment which consists of a standard round wire staple with flat plates or wings 30 attached to the proximal portion of the legs. FIG. 9 shows another staple similar to that of FIG. 9 which is manufactured from flat metal stock and bent. Again the staple legs include wings 30 such that the height of these wings is significantly greater than the height of the penetrative portion 16 of the staple legs.

Figure 10:
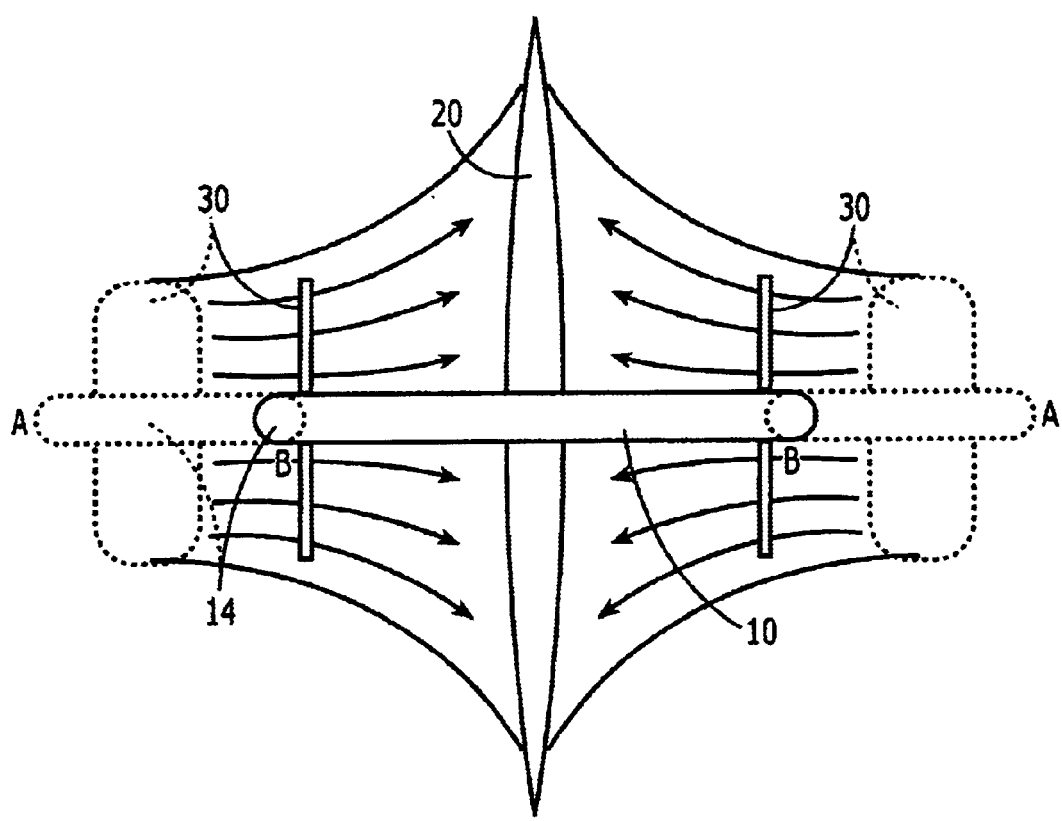
FIG. 10 is a plan view of the staple of FIG. 9 in position across a tissue opening.
Figure 11:
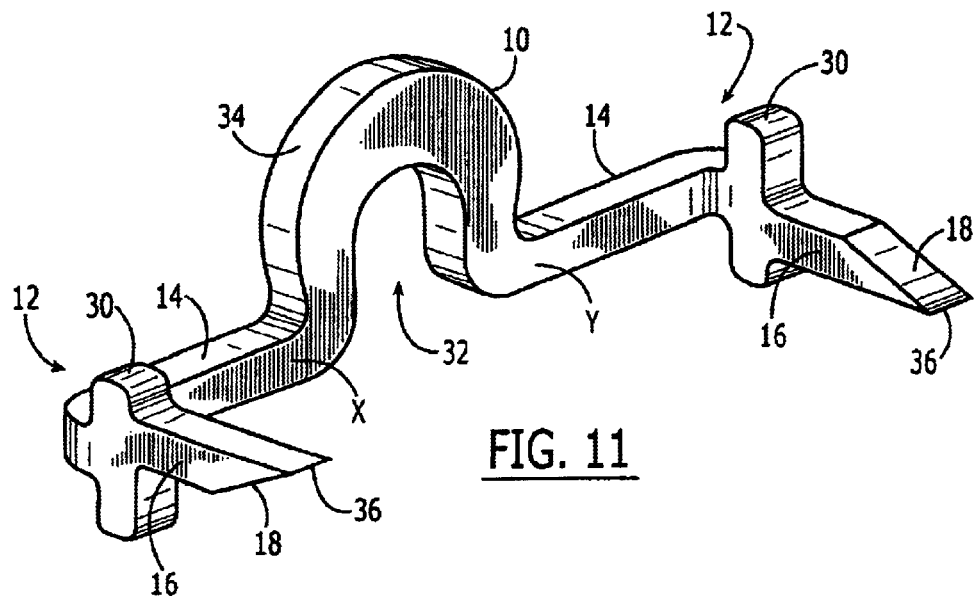

The process by which these improved staples achieve greater areas of compression over the length of an opening in body tissue is illustrated in FIG. 10. FIG. 11 shows a staple of the kind illustrated in FIG. 9 but the same principle applies to all the staples of FIGS. 5 to 9. It can be seen that as the staple legs move from their open position at 'A' to their closed position at 'B' tissue 24 is compressed ahead of the wings 30 and this compression radiates over a much greater length of the slit or opening 20 than would be the case if the wings were not attached to the staple legs.

FIG. 11 shows a staple stamped from a flat sheet and bent into its initial configuration (rather than a wire staple as previously described). The base 10 of the staple is horseshoe shaped rather than a flat linear base. The horseshoe shape defines a "U"-shaped opening 32 which allows the staple to sit on top of a blood locator tube extending from the end of a stapler. Such a stapler is described in WO 02/19922.

The stapler of WO 02/19922 takes the form of a hollow shaft and a blood locator tube slidable axially within the shaft. The tube projects beyond the end of the shaft to enter a puncture site in a blood vessel, and blood flowing back through the tube and exiting the device indicates to the surgeon that the tip of the shaft (where the stapling head is located) is at the incision in the vessel. A surgical staple straddles the tube and is slidable thereon forwardly towards an anvil against which the staple may be deformed to staple together the opposite edges of the puncture site. A cam mechanism drives the staple forwardly along the tube into deforming engagement with the anvil and at the same time retracts the tube into the shaft in time to allow the legs of the staple to close onto the puncture site.

The staple of FIG. 11 is adapted for use with such a device in that "U"-shaped opening 32 is adapted to straddle and slide on the blood locator tube.

The staple has a pair of legs 12 extending from the ends of the base 10. Each leg is generally "L"-shaped in plan view and comprises a proximal portion 14 and a distal portion 16 terminating at a pointed tip 18. In use (see also FIG. 12), the base 10 is held by an anvil (not shown) while forming arms of the stapler (not shown) push the proximal portions forwardly deforming the staple at bend points X and Y. The blood locator tube is withdrawn during this formation to ensure that as the tips 18 approach one another (ultimately coming to rest in the configuration of FIG. 12), they do not catch the locator tube.

Located on the distal portion 16 is a compressive portion 30 in the form of a bar extending at right angles to the distal portion. In this staple, therefore, the compressive portion and the penetrative portion are both located on the distal portion of the "L"-shaped leg. The penetrative portion is the part of the leg extending from the bar 30 to the tip 18. The forward surface 30a of the bar provides a shoulder acting as a depth stop to prevent the leg penetrating the vessel wall too deeply. This feature can be used to ensure that the tip will not penetrate into the lumen of a blood vessel by designing the staple such that the distance between the front surface 30a and the extremity of the tip 18 is less than the vessel wall thickness. The bar also serves as a compressive feature spreading the compressive forces provided by the staple along a length of the incision corresponding to the height H of the bar 30 (FIG. 12) as opposed to just the lesser height h of the penetrative portion. The compression is also increased by the relatively small distance between the bars 30 when the staple is closed.

By making the staple from a sheet material rather than from wire, another significant advantage is obtainable. The thickness of the material of the base (measured between the internal surface of the opening 32 and the corresponding external surface 34) is not constant but instead increases to a maximum at the apex of the horseshoe. This strengthens the structure against a tendency for the curve to distort as the staple is being formed. It has been found that the action of the former and anvil bending the legs relative to the base tends to cause the horseshoe curve to open out or flatten somewhat. It will be appreciated that this can lead to the staple deploying incorrectly, as the legs tend to deviate from the "straight-ahead" orientation during closure. Adding extra material to the curve toward the top selectively reinforces the curve at this point of maximum strain during forming and counteracts the tendency to distort.

Figure 12:
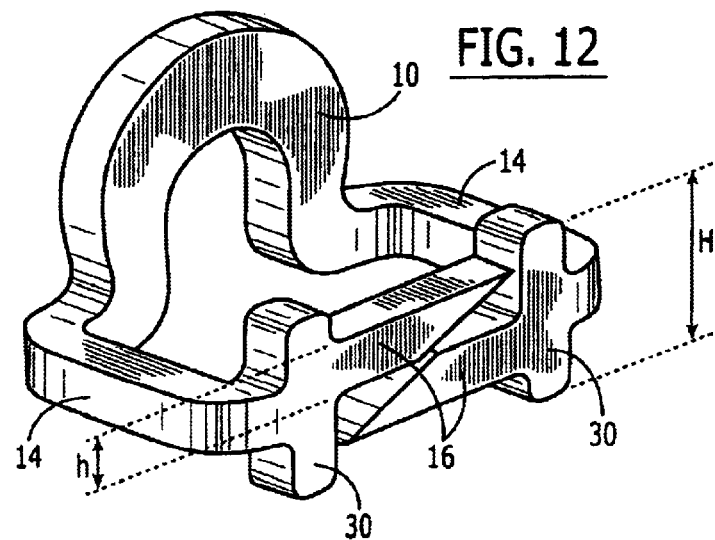

Another important feature of the staple of FIGS. 11 and 12 is that the staple is not symmetrical about the centre line. The penetrative portions 16 are staggered vertically relative to one another so that one is disposed slightly above the line of the proximal portions and the other slightly below this line.

In addition, the respective tips 18 are bevelled oppositely to one another so that the leading edge 36 of the tip on the left-hand penetrative portion (as viewed in FIG. 11) is significantly above the leading edge 36 of the right-hand tip. This double offset (staggering the respective penetrative portions and reversing the bevelling of the tips) allows the two legs to close completely, so that the tips approach one another and pass one another when the staple is formed, providing greater compression and more reliable closure.

Figure 13:
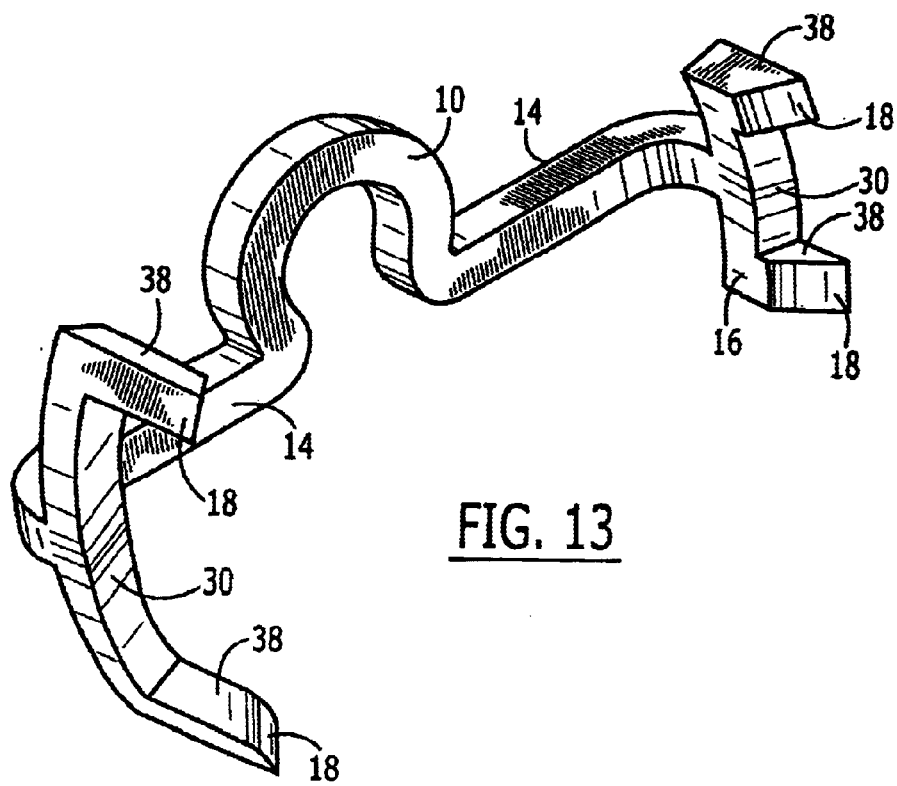
Figure 14:
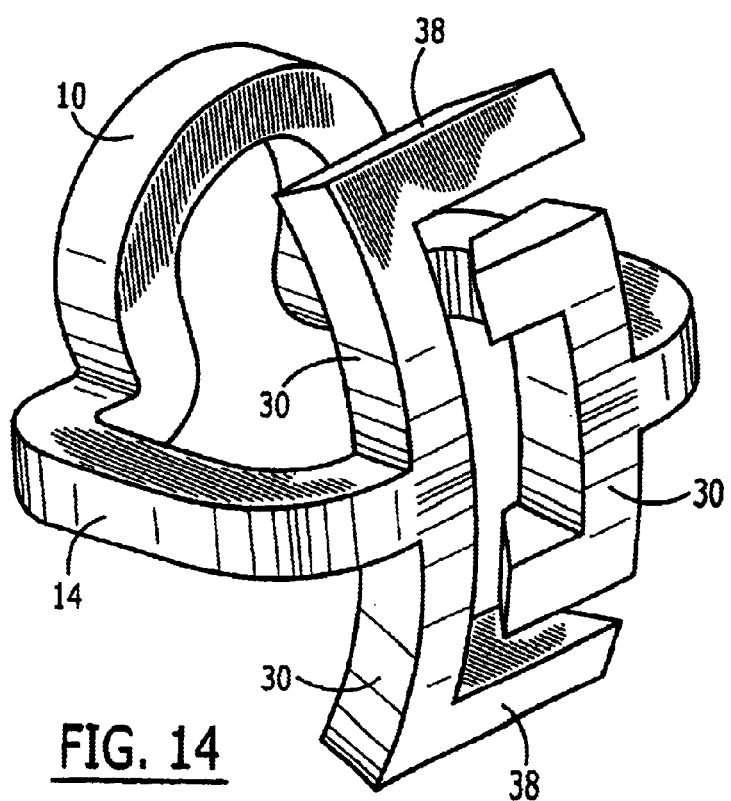

FIGS. 13 and 14 show a further embodiment of staple in open and closed configurations. The staple again has a base 10 with a leg 12 extending from each end. The base is horseshoe shaped, but in this case rather than there being additional material at the apex of the horseshoe curve, the curve assumes a slight omega ($\Omega$) shape with the ends of the curve pointing inwards to counteract straightening tendencies.

Each leg 12 branches to a pair of tips 18 each having a penetrative portion 38. The two penetrative portions on each leg extend from the ends of a respective compressive portion 30 in the form of a curved bar which is generally perpendicular to both the proximal portion 14 and the penetrative portions 38. The bar 30 provides a shoulder acting as a depth stop and acts to spread the compressive forces of the staple along its length.

It can be seen from FIG. 14 that the legs are once again asymmetrical with respect to one another. The penetrative portions 38 of the left-hand leg are both longer and further separated from one another than those of the right-hand leg. Again this ensures that the two legs do not interfere with one another during closure and that the staple can form a fully closed structure when viewed in plan (see by comparison FIG. 2C in which there is a gap between the respective tips of the prior art staple, and the curve appears open in plan as a consequence.

The reason for the curvature of the bars 30 in the embodiment of FIGS. 13 and 14 is that the stapler for which it is designed has a round profile. In general it is desired to make the cross-sectional area of the stapler shaft as small as possible to minimise trauma arising from the introduction of the stapler. The shape of this embodiment of staple therefore allows the staple to fit in a rounded shaft while allowing the compressive portions (bars 30) to grip the sides of the wound as widely as possible, as will be appreciated with reference to FIG. 10.

Figure 15:
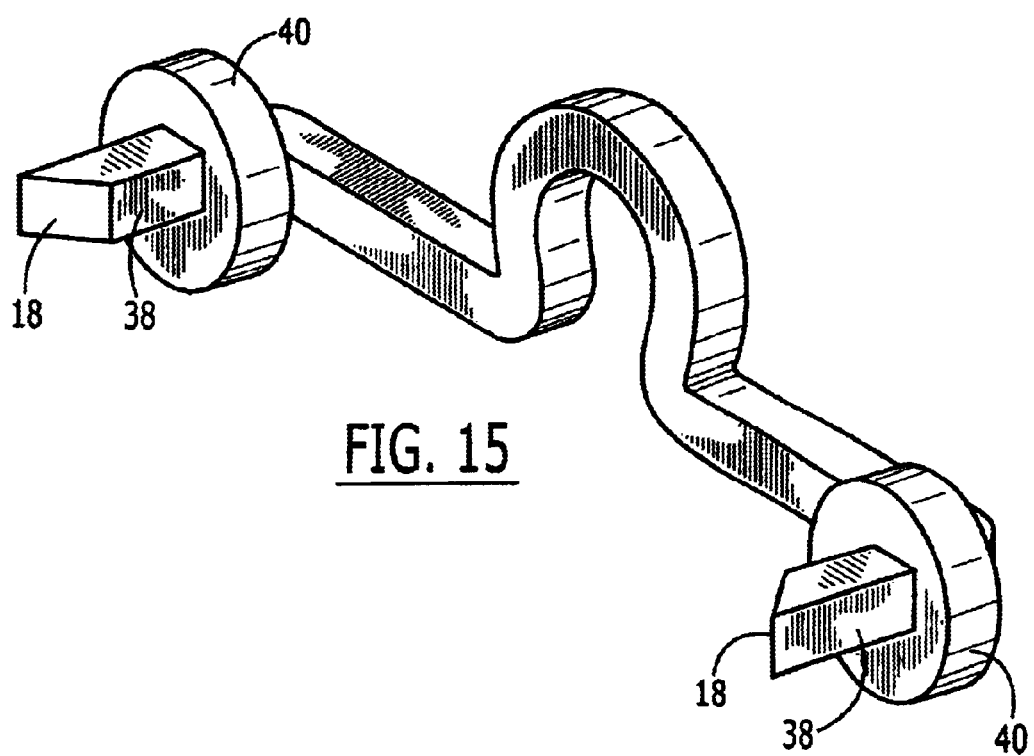
Figure 16:
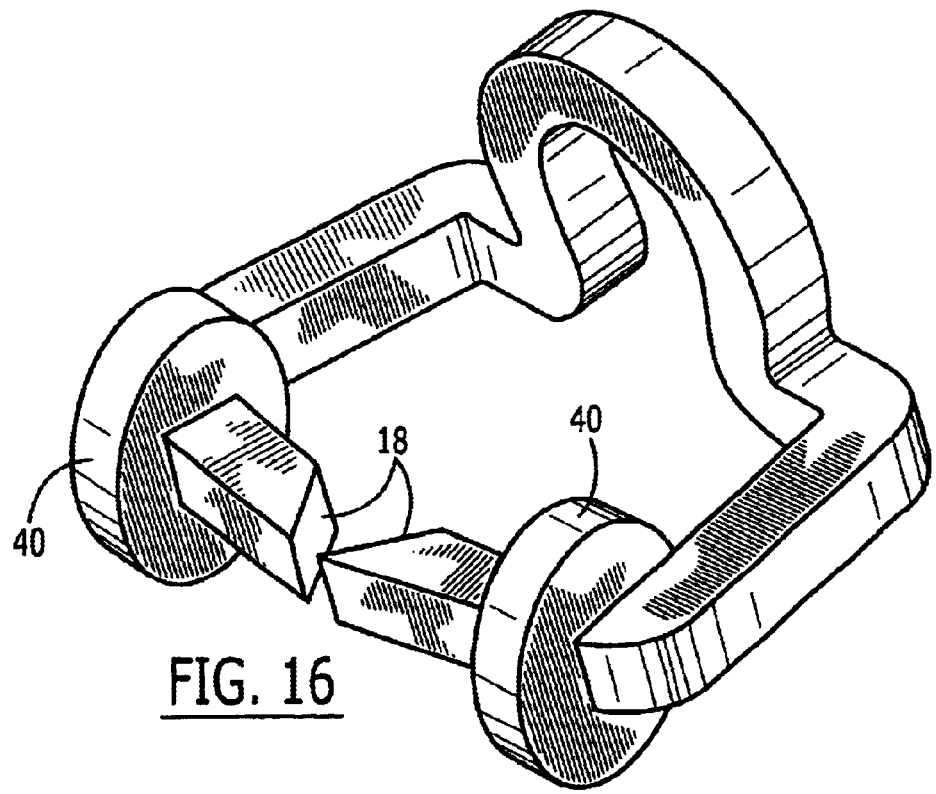

FIGS. 15 and 16 provide yet another embodiment in which the penetrative portions 38 of the legs 12 extend between the tip 18 and a shoulder of a compressive portion of the leg which in this case is provided by a disk 40 mounted on the distal portion of each leg.

The embodiments described herein have "L"-shaped legs with a roughly 90° angle between proximal and distal sections. It will be noted that the compressive section can be on either the proximal section or the distal section. Furthermore, the legs need not take this "L"-shape and can instead be curved (e.g. in a quarter-circle), with the portion of leg adjacent the tip defining a penetrative portion and a compressive structure being located further along the curve towards the base.

To aid in staple formation the point at which the legs join the base can be weakened or provided by a notch, but in most cases this is unnecessary as the deformation between the anvil and former will cause the legs to bend correctly at the junction with the base.

The invention is not limited to the embodiments described herein which may be modified or varied without departing from the scope of the invention.

What is claimed is:

1. A surgical staple comprising a base and a pair of legs each extending from an opposite end of the base, each leg having a penetrative portion terminating at a tip, the staple being deformable at a bend point on each leg to bend each leg relative to the base causing each tip to approach the other leg along a substantially arcuate path, wherein each leg further comprises a compressive portion located between a proximal portion of the leg extending from the base and the penetrative portion, and each compressive portion extending transverse to a plane containing said proximal portion such that each compressive portion has a height greater than a height of said proximal portion of said legs.

2. A surgical staple as claimed in claim 1, wherein the compressive portion has a cross-sectional area greater than that of the penetrative portion.

3. A surgical staple as claimed in claim 1, wherein the compressive portion comprises a shoulder from which the penetrative portion extends.

4. A surgical staple as claimed in claim 3, wherein the shoulder is defined by an elongate member disposed substantially perpendicular to the penetrative portion.

5. A surgical staple as claimed in claim 1, wherein each leg branches to two or more penetrative portions each terminating at a respective tip, the penetrative portions being connected by said compressive structure.

6. A surgical staple as claimed in claim 5, wherein each compressive portion is in the form of a bar extending substantially perpendicular to the proximal portion of the leg, and said penetrative portions extending from the ends of said bar substantially perpendicular thereto.

7. A surgical staple as claimed in claim 1, wherein each leg is generally "L"-shaped having a proximal portion connected to the base and a distal portion including said penetrative portion, said proximal and distal portions being connected at an angle of about 70–110 degrees and lying substantially within the same plane.

8. A surgical staple as claimed in claim 7, wherein said angle is approximately 90 degrees.

9. A surgical staple as claimed in claim 7, wherein the penetrating portions are round in cross-section and the compressive portions are substantially flat in cross-section.

10. A surgical staple as claimed in claim 9, wherein the staple is formed from a length of round wire and said compressive portions are formed by flattening a length of said wire forming part of each leg.

11. A surgical staple as claimed in claim 10, wherein the flat portions are plates attached to a round wire staple.

12. A surgical staple as claimed in claim 1, wherein the staple is cut from flat metal stock and bent.

13. A surgical staple as claimed in claim 1, wherein the compressive portions comprise sections of elongate material bent out of alignment with the penetrative portions.

14. A surgical staple as claimed in claim 13, wherein the bent portions are sinusoidal.

15. A surgical staple as claimed in claim 1, wherein the legs are divided and opposite divisions bent in opposite directions to provide said compressive portions.

16. A surgical staple as claimed in claim 1, wherein the penetrative portion on one leg is staggered from the penetrative portion of the other leg, whereby the staple is deformable in a manner which allows the respective tips to approach and pass one another, each moving along a different but substantially parallel plane.

17. A surgical staple as claimed in claim 1, wherein the base is in the form of a horseshoe shape extending substantially transverse to the plane containing the proximal portion of each leg.

18. A surgical staple as claimed in claim 17, wherein the thickness of the base varies about the curve of the horseshoe shape, with a greater thickness at the apex than at the sides.

19. A surgical staple, comprising a base having first and second legs extending therefrom and bendable relative to the base at opposed ends of the base, each leg including a distal tissue penetrating tip formed thereon and a compressive member formed proximal to the distal tissue penetrating tip and having a size adapted to prevent passage of tissue there over when the distal tissue penetrating tips are inserted through tissue and bended relative to the base, wherein each leg including a proximal portion that is proximal to the compressive member and each compressive member extends in a direction substantially transverse to a plane containing said proximal portion of each leg such that each compressive member has a height that is greater than a height of said proximal portion of each leg.

20. The surgical staple of claim 19, wherein the base includes at least one arc formed therein.

21. The surgical staple of claim 19, wherein the distal tissue penetrating tip on each leg comprises first and second penetrating tips, and wherein the compressive member connects the first and second penetrating tips on each leg.

22. A surgical staple, comprising a base portion having first and second leg portions extending from opposed terminal ends thereof, each leg being bendable at a bend point, and each leg including a compressive member formed thereon at a location between the bend point and a tissue piercing tip formed on the leg, wherein each leg including a proximal portion that is proximal to the compressive member and each compressive member extends substantially transverse to a plane containing said proximal portion of each leg such that each compressive member has a height that is greater than a height of said proximal portion of each leg.

23. A surgical staple, comprising a base having at least one curve formed therein, and a pair of legs extending from opposite ends of the base, each leg including a proximal portion bendable relative to the base, and a distal portion having a pair of tissue penetrating tips that are connected by a compressive bar, each compressive bar having a height that is greater than a height of the proximal portion of the leg, the heights being measured in a direction perpendicular to a plane containing the proximal portion of the leg.

24. The surgical staple of claim 23, wherein the base extends in a plane that is substantially perpendicular to each plane containing the distal portion of each leg.

* * * * *